Figure 1:
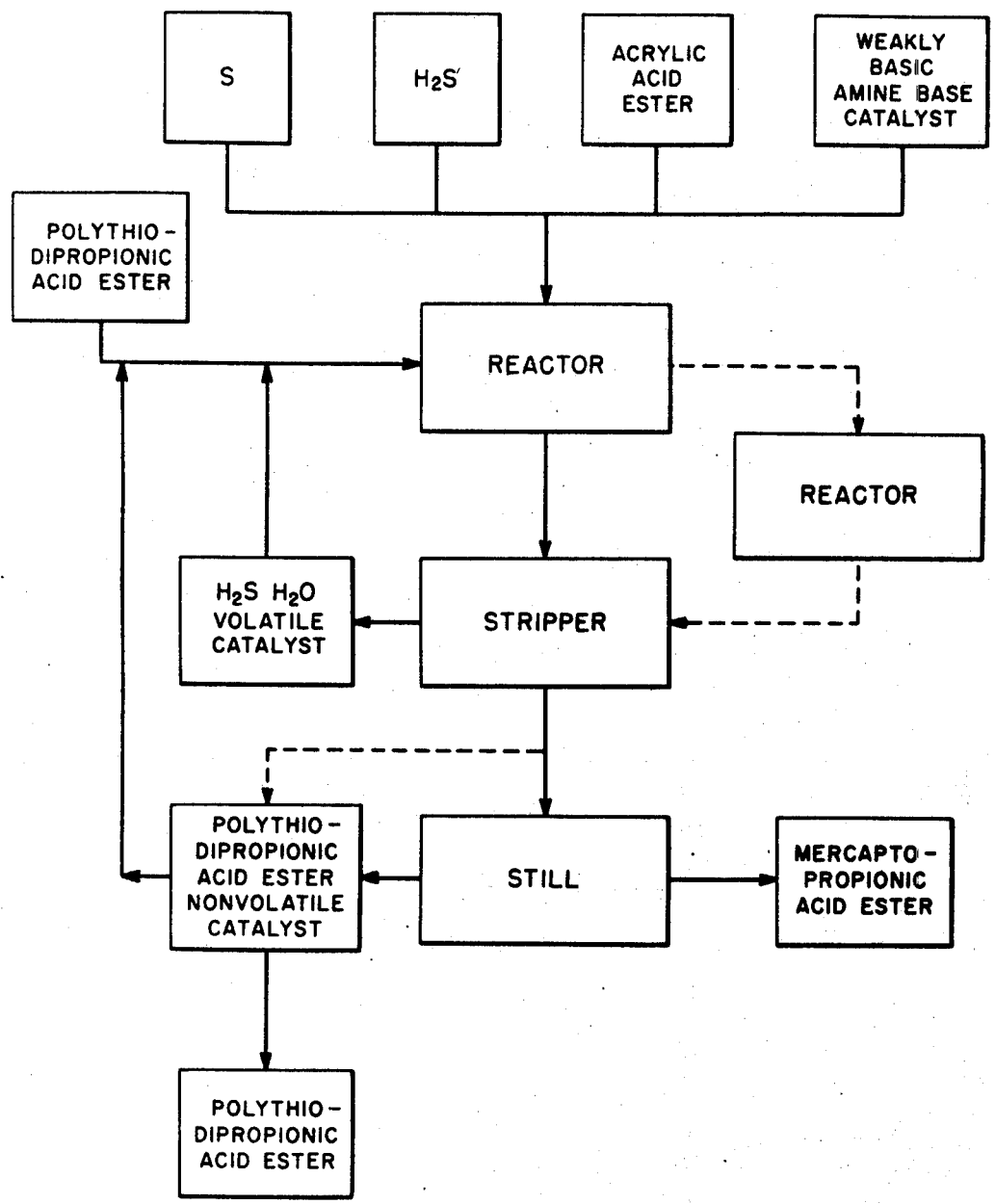

United States Patent [19]

Gladstone et al.

[11] 4,067,901

[45] Jan. 10, 1978

[54] METHOD FOR PREPARING MERCAPTO PROPIONIC ACID ESTERS AND POLYTHIO DIPROPIONIC ACID ESTERS

[75] Inventors: Shaul Gladstone, Arden, Del.; Srinivasa R. Rao, Ridgewood, N.J.; C. Joseph Rosshirt, Luling, La.

[73] Assignee: Witco Chemical Corporation, New York, N.Y.

[21] Appl. No.: 795,677

[22] Filed: May 11, 1977

Related U.S. Application Data

[63] Continuation-in-part of Ser. No. 614,828, Sept. 19, 1975, which is a continuation-in-part of Ser. No. 380,006, July 17, 1973, abandoned.

[51] Int. Cl.$^2$ .................. C07C 148/00; C07C 149/20

[52] U.S. Cl. ...................................... 560/147; 560/154
[58] Field of Search ..................... 260/481 R

[56] References Cited

FOREIGN PATENT DOCUMENTS

| 1,485,266 | 5/1967 | France | 260/526 S |
| 40,151 | 7/1965 | Japan | 260/481 R |

*Primary Examiner*—Vivian Garner

[57] ABSTRACT

A process is provided for the preparation of mercapto propionic acid esters and/or polythio dipropionic acid esters by reaction of an acrylic acid ester with hydrogen sulfide in the presence of a weakly basic amine as a catalyst, a polythiodipropionic acid ester as a reactive solvent, and added elemental sulfur.

25 Claims, 1 Drawing Figure

METHOD FOR PREPARING MERCAPTO PROPIONIC ACID ESTERS AND POLYTHIO DIPROPIONIC ACID ESTERS

This application is a continuation-in-part of Ser. No. 614,828, filed Sept. 19, 1975, which in turn is a continuation-in-part of Ser. No. 380,006, filed July 17, 1973, and now abandoned.

Dithiodipropionic acid esters have been prepared by oxidation of mercaptans followed by esterification, as disclosed in U.S. Pat. Nos. 2,530,882 and 3,501,520, and by reaction of mercaptans with propionic acid chloride, as disclosed in U.S. Pat. Nos. 2,530,882 and 2,719,170. Monothiodipropionic acid esters are obtained by similar procedures.

When starting with acrylic acid esters, the preparation of mercapto propionic acid esters has been difficult to achieve, and the resulting product usually has been a thioether. Ammonium or sodium sulfide, hydrosulfide and polysulfide has been used as a reactant in these procedures, and the reactions have been carried out in aqueous media, in which the sulfide is soluble. It is difficult to isolate the monothiodipropionic acid ester (R-S-R) from the dithiodipropionic acid ester (R-S-S-R) which are simultaneously formed in these reactions, and tri- and tetrathiodipropionic acid esters may also be formed, which further complicates recovery procedures.

Dutch Patent No. 65 08954 describes the reaction of acrylic acid and hydrogen sulfide in the presence of an organic base to form β-mercaptopropionic acid. The hydrogen sulfide is used in the liquid phase under a sufficiently high pressure to ensure that it is a liquid. Quite high pressures, of the order of from 8 to 15 atmospheres, are required, as shown in the working Examples. The organic base is used as the catalyst in a stoichiometric amount, ranging from 1.01 to 1.1 moles per mole of acrylic acid, and the hydrogen sulfide is used in an amount of from 1.5 to 10 moles per mole of acrylic acid. No solvent is used.

Japanese Patent No. 40151/70 prepared sulphur-containing mono and dialiphatic acids and esters by reacting acrylic or methacrylic acid or their esters in the presence of a small amount of alkaline catalyst under normal or elevated pressure with hydrogen sulfide. The result was the formation of sulphur-containing acids of the types:

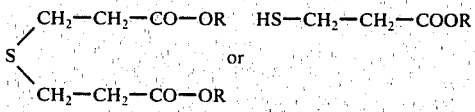

In the Example given, methyl acrylate is reacted in the presence of trimethylbenzyl ammonium hydroxide, the reaction mixture being shaken in a sealed vessel with 10 atmospheres of hydrogen sulfide. The resultant reaction product has a very small amount (2g) of methylmercaptopropionate, and a relatively large amount (43 g) of dimethyl-thiodipropionate. No solvent is used, and rather high pressures, of the order 10 atmospheres of hydrogen sulfide, are employed.

In accordance with Ser. No. 614,828, filed Sept. 19, 1975, it has been determined that mercaptopropionic acid esters and/or dithio dipropionic acid esters and higher polythio dipropionic acid esters can be formed in high yields by reaction of acrylic acid esters with hydrogen sulfide in the presence of a weakly basic amine catalyst and a polythiodipropionic acid ester in an amount of at least 30% by weight of the total of monothiodipropionic acid ester and polythiodipropionic acid ester present. The polythiodipropionic acid ester is reactive, and takes part in the reaction, with a material improvement in the course of the reaction, and particularly in the yield of the mercapto propionic acid ester, when the amount of polythiodipropionic acid ester is at least 30% by weight.

The overall reaction for preparing mercapto propionic acid ester can be set forth by the following equation.

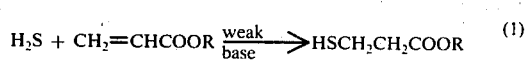

In this reaction (1) and in reactions (2), (3), (4), and (5), R is a hydrocarbon group, alkyl, cycloalkyl, or alkylcycloalkyl, having from one to eight carbon atoms.

Under the conditions of the process of the invention, the above reaction is favored, and the mercaptopropionic acid ester is obtained in good yield.

However, the reaction system is extremely complex. A number of other reactions take place concurrently, some of which have been verified, and some of which are postulated from the reaction products that are obtained in the course of the reaction. Under controlled conditions other than those specified for the preparation of mercaptopropionic acid ester, the balance of the reactions can be shifted, in favor of entirely different reaction products. If desired, the reaction conditions can be so controlled that the predominant reaction product is not mercaptopropinic acid ester but dithiodipropionic acid ester, and higher polythiodipropionic acid esters, together with by-products, such as monothiodipropionic acid esters. The process of the invention can be directed to produce dithiodipropionic acid esters and polythiodipropionic acid esters in good yield, and minimize the formation of by-products monothiodipropionic acid esters.

In one important concurrent and consequential side reaction, the mercaptopropionic acid ester reacts with acrylic acid ester to form a monothiodipropionic acid ester, in accordance with the following reaction.

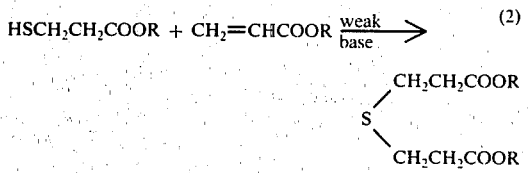

This product is not desired, and reduces the yield of the products that are desired.

It is apparent from reaction (2) that in the preparation of the mercaptopropionic acid ester, it is desirable to remove the ester as soon as possible, preferably as rapidly as it is formed, from the reaction system, so as to avoid reaction of the product with the acrylic acid ester to form the monothiodipropionic acid ester.

It is believed that the following correlated reaction sequence, results in the overall reaction indicated in (1) above. First, the dithiodipropionic acid ester reacts with hydrogen sulfide, in accordance with the following equilibrium scheme:

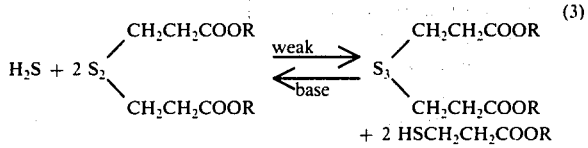

(3)

It is for this reason that the dithiodipropionic acid ester solvent is referred to as a reactive solvent. It clearly takes part in the reaction, and can lead to an increase in yield.

This is followed by reaction of the hydrogen sulfide and acrylic acid ester with the trithiodipropionic acid ester thus formed.

$$2CH_2=CH-CO-OR + H_2S + S_3(CH_2CH_2-CO-OR)_2 \rightarrow 2S_2(CH_2CH_2CO-OR)_2 \quad (4)$$

It appears that the acrylic acid ester appears to react with hydrogen sulfide more readily in the presence of trithiodipropionic acid ester than with the mercapto compounds present in the reaction mixture. The presence of some sulfur, therefore, ensures that polythiodipropionic acid ester is present initially. Addition of small quantities of sulfur either continuously or from time to time helps to maintain a small concentration of trithiodipropionic acid ester at all times.

Therefore, in this complex system, elemental sulfur has an important and in some respects essential effect. The effect of sulfur is essential if higher polythiodipropionic acid esters are desired. In amounts less than this, sulfur will enhance the yield of mercapto propionic acid ester and diminish the yield of the undesired monothio dipropionic acid ester, which can be important when mercaptopropionic acid ester is the desired product.

The formation of the higher polythiodipropionic acid esters proceeds by the following reactions.

The mercaptopropionic acid ester can react with sulfur in the presence of the weakly basic amine catalyst, such as ammonia, to form dithiopropionic acid ester and higher polythiodipropionic acid ester, according to the amount of sulfur.

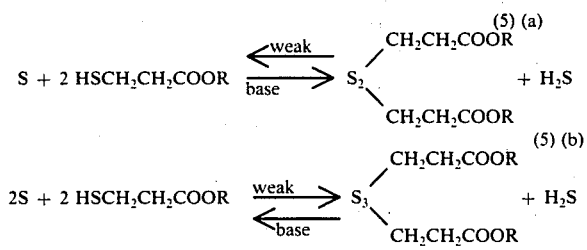

(5) (a)

(5) (b)

Sulfur also reacts with dithiopropionic acid ester to form trithio and higher polythiodipropionic acid esters:

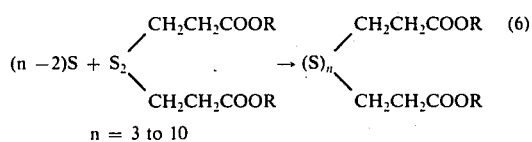

(6)

n = 3 to 10

In general, an amount of sulfur within the range from about 0.01 to about 0.5 and preferably from about 0.03 to about 0.05 mole per mole of acrylic acid ester decreases the proportion of monothio dipropionic acid ester, and enhances the ratio of dithio dipropionic acid ester plus mercaptopropionic acid ester to the monothio dipropionic acid ester. At amounts in excess of 0.05 mole, and especially in excess of 0.5 mole per mole of acrylic acid ester, the total proportion of dithiodipropionic acid ester and higher solythiodipropionic acid ester increases. At amounts of from 0.5 to 1 mole of sulfur per mole of acrylic acid ester, a mixture of dithio and trithiodipropionic acid ester is formed; at amounts of sulfur of from 1 to 1.5 mole per mole of acrylic acid ester, a mixture of tri and tetrathiodipropionic acid ester is formed; and so on, up through the polythiodipropionic acid ester series. An amount of 4.5 moles of sulfur corresponds to decathiodipropionic acid ester. A practical upper limit is 5 moles of sulfur per mole of acrylic acid ester.

The process of the invention is illustrated in the flow sheet represented by FIG. 1 which shows the formation of the principal reaction products of the process, alternatively, sequentially, or simultaneously: mercapto propionic acid ester and dithiodipropionic acid ester or higher polythiodipropionic acid ester, starting from hydrogen sulfide, acrylic acid ester, the weakly basic amine catalyst, and sulfur.

The reactants are blended together in the proportions to give the desired product in a reactor, where they are held under conditions controlled to form the desired product. If desired, several reactors can be used in series or in parallel, and the addition of one such in-series reactor is shown by the alternative dashed lines in the flow sheet.

The completed reaction product is transferred to a stripper, where the unreacted hydrogen sulfide and any volatile catalyst, together with any water, are removed. The residue is composed of mercaptopropionic acid ester, the solvent, dithio or polythio dipropionic acid ester, any nonvolatile catalyst and other by-products, as shown in the above equations.

If mercaptopropionic acid ester is to be isolated as the reaction product, the residue from the stripper is transferred to a still, where the mercaptopropionic acid ester is distilled off in vacuo. The residue, which also contains any nonvolatile catalyst, can then be recycled as a solvent for the reaction to the reactor.

If the desired product is the dithio or polythio dipropionic acid ester, then the residue from the stripper need not be transferred to a still, but instead can be worked up by removal of any nonvolatile catalyst as the desired product, since under the reaction conditions appropriate for formation of the dithio or polythio dipropionic acid ester, the mercaptopropionic acid ester will be present only in negligible amounts.

The operation of the process can be continuous or batchwise, as may be preferable according to available equipment.

Experimental evidence tends to show that the reaction of mercaptopropionic acid ester with acrylic acid ester (reaction (2) above) is favored by a higher temperature, more so than the reaction of acrylic acid ester and hydrogen sulfide. Accordingly, a low reaction temperature favors the formation of mercaptopropionic acid ester, while at higher reaction temperatures the formation of dithio and polythio dipropionic acid esters is favored. Accordingly, low reaction temperatures are used when the mercaptopropionic acid ester is the desired product. Since dithio and/or polythio dipropionic acid esters are formed at both low and high reaction temperature and mercaptopropionic acid ester formed is converted to the dithio and higher polythio dipropionic acid esters, both low and high reaction temperatures can be used when these are the desired products.

In general, reaction temperatures within the range from about 0° to about 40° C are preferred for mercaptopropionic acid ester formation. However, significant amounts of mercaptopropionic acid ester are formed at reaction temperatures up to about 75° C.

At reaction temperatures in excess of 40° C, significant quantities of the monothiodipropionic acid ester begin to be formed, and at temperatures within the range from about 60° C to about 150° C, reaction (2) consumes an increasing proportion of mercaptopropionic acid ester, formed in reaction (1). Thus, while reaction temperatures within the range from about 0° to about 150° C can be used, the higher reaction temperatures within the range from about 75° to about 150° C may be preferred when the dithio and/or polythio dipropionic acid esters are desired products.

The formation of mercaptopropionic acid ester is also favored by a high hydrogen sulfide:acrylic ester molar ratio. If the hydrogen sulfide:acrylic ester molar ratio falls below 1:1, then reaction (1) is slowed in proportion to reaction (2), and relatively large amounts of the monothiodipropionic acid ester are obtained in reaction (2).

Accordingly, if the mercaptopropionic acid ester is the desired reaction product, the amount of hydrogen sulfide is in excess of the stoichiometric amount of 1:1 ratio, and preferably in the ratio of 1.25:1 to 5:1 $H_2S$ to acrylic acid ester, required in reaction (1). If the dithio or polythio dipropionic acid ester is a desired intermediate or end product, the proportion of hydrogen sulfide is less than this, within the range from 0.5:1 to 1:1. and enough sulfur is added to convert the initially formed mercaptopropionic acid ester to the desired dithio or polythio dipropionic acid ester according to reactions (3) and (4).

Since hydrogen sulfide is a gas, and is soluble in the reaction system only to a limited amount, ranging up to 3% by weight at atmospheric pressure and temperature, it may be desirable to carry out the reaction under a superatmospheric pressure of hydrogen sulfide, especially if mercaptopropionic acid ester is the desired product, since this has the effect of increasing the proportion of hydrogen sulfide in the reaction system. Accordingly, relatively high hydrogen sulfide pressures can be used, ranging up to about 500 psig. The reaction will proceed at atmospheric pressure, however, and normally the pressure will be within the range from atmospheric pressure to about 200 psig. The $H_2S$ concentration is within the range from about 0.1% to saturation in the reaction solvent under the reaction conditions.

The residence time is in no way critical. The reaction proceeds rather rapidly at elevated temperatures, more slowly at lower temperatures. The reactants are of course kept in contact until an acceptable yield of the desired product is obtained. The residence time is normally within the range from about 10 minutes to about 5 hours, and preferably within the range from about ½ hour to about 2 hours, under the reaction conditions set forth above.

The reaction with $H_2S$ proceeds with any acrylic acid ester having from one to about eight carbons in the ester substituent, such as methyl acrylate, ethyl acrylate, propyl acrylate, isopropyl acrylate, butyl acrylate, isobutyl acrylate, sec-butyl acrylate, tert-butyl acrylate, amyl acrylate, isoamyl acrylate, hexyl acrylate, heptyl acrylate, octyl acrylate, isooctyl acrylate and 2-ethylhexyl acrylate.

The reaction proceeds in the presence of a weakly basic amine catalyst, including ammonia and organic amines, both the open chain or aliphatic and cyclic amines, and the cyclic amines include the heterocyclic amines with the nitrogen atom in the ring, and the carbocyclic amines with the amine nitrogen attached to the ring.

By "weakly basic" it is meant that the amine is more alkaline than aniline and less alkaline than alkali metal hydroxide. The "weakly basic" amine catalysts that are effective in the process of the invention react reversibly with $H_2S$ in the way that ammonia and $H_2S$ make ammonium sulfide which readily regenerates $H_2S$ and ammonia on heating. Less basic materials (e.g. aniline) do not react with $H_2S$ and strong bases react with $H_2S$ irreversibly. Quaternary bases are often thought of as strong bases but are decomposed by heating so that their reaction with $H_2S$ is also reversible.

Ammonia can be used as ammonia gas or, conveniently, in aqueous solution as ammonium hydroxide or ammonium sulfide. The concentration of ammonia in the catalyst is not critical, and is normally within the range from about 20 to about 100%. Any desired concentration can be used, since the important factor is not the ammonia concentration in ammonium hydroxide, but the proportion of ammonia in the reaction system which is suitably from about 0.1% to about 10% by weight as $NH_3$.

The organic amines that can be used are defined by the formula.

(a)

Quaternary amines can also be used, as defined by the formula.

(b)

In the above formulae, $R_1$, $R_2$, and $R_3$ represent hydrogen or hydrocarbon groups having from one to about eighteen carbon atoms in the organic amine of formula (a) and at least one R is not hydrogen, and $R_4$, $R_5$, $R_6$ and $R_7$ are hydrocarbon groups having from one to eighteen carbon atoms. The R groups may be taken singly, as alkyl, cycloalkyl, cycloalkyl alkyl, and alkaryl groups, or two or more R groups may be taken together with the nitrogen to form a heterocyclic ring with the nitrogen atom in the ring.

While the R groups individually may have up to 18 carbon atoms, the R groups in the amine or quaternary amine should not in the aggregate total more than 30 carbons.

X represents hydrosulfide $HS^-$, or sulfide $S^{--}$, or any basic anion of the inorganic or organic type, such as $OH^-$, $HCO_3^-$, $CO_3^{=}$, $HCOO^-$, and $CH_3COO^-$.

The R substituents may also include one or more hydroxy groups —OH and/or one or more ether groups —O—, and/or one or more ester groups —COOR.

Exemplary R alkyl groups include methyl, ethyl, propyl, isopropyl, butyl, isobutyl, tertiary butyl, amyl, isoamyl, hexyl, isohexyl, heptyl, isoheptyl, octyl, tertiary-octy, 2-ethylhexyl, isooctyl, nonyl, decyl, dodecyl, hexadecyl, tridecyl, tetradecyl and octadecyl. R alkenyl groups include propenyl, butenyl, pentenyl, hexenyl, heptenyl, octenyl, nonenyl, decenyl, dodecenyl, ricinoleyl, linoleyl, and linolenyl.

Hydroxyl-containing alkyl groups include hydroxyethyl, hydroxypropyl, hydroxybutyl, hydroxyamyl and hydroxyhexyl. As the alkyl substituent to which the hydroxyl is attached becomes longer than six carbon atoms, the effect of the hydroxyl group lessens, and becomes almost negligible.

Ether-containing alkyl groups include ethoxyethyl, ethoxypropyl, propoxypropyl, butoxyethyl, amyloxyamyl, decyloxyethyl, dodecyloxyethyl, and octyloxyoctyl.

Ester-containing groups include carboethoxy methyl, carbomethoxy ethyl, and carboethoxy ethyl.

Cycloalkyl R groups include cyclopropyl, cyclobutyl, cyclopentyl, cyclohexyl, cycloheptyl and cyclooctyl.

Heterocyclic groups in which two Rs are taken together to form a heterocyclic ring which contains the nitrogen in the molecule include piperidine, pyridine, pyrrolidine, pyrazolidine, piperazine, triethylenediamine and pyrrolizine, morpholine, N-methyl morpholine, N,N-dimethyl piperazine and N-ethyl morpholine.

Exemplary amines include methyl amine, ethyl amine, propyl amine, isopropyl amine, butyl amine, amyl amine, hexyl amine, heptyl amine, octyl amine, decyl amine, dodecyl amine, myristyl amine, palmityl amine, stearyl amine, monoethanolamine; dimethyl amine, methyl ethyl amine, diisopropyl amine, dibutyl amine, dihexyl amine, dioctyl amine, butyl hexyl amine, didecyl amine, didodecyl amine, propylamyl amine, diethanolamine, dipropanolamine, dihexanolamine; trimethyl amine, triisopropyl amine, tributyl amine, methyl diethyl amine, dimethyl ethyl amine, methyl ethyl propyl amine, triamyl amine, triisobutyl amine, trihexyl amine, trioctyl amine, tridecyl amine, methyl hexyl decyl amine, dodecyl dimethyl amine, octadecyl dimethyl amine, triethanolamine, triisopropanolamine, tributanolamine, diethyl cyclohexylamine, dimethyl ethanol amine; cyclohexyl amine, dicyclohexyl amine, methyl cyclohexyl amine, ethyl cyclopentyl amine, tricyclohexyl amine, dicyclopentyl hexyl amine, cyclopropyl methyl amine, cycloheptyl amine, cyclopentyl amine, tetramethyl-1,4-butane diamine, ethylene diamine, diethylene triamine, tetramethyl ethylene diamine, N-tetradecyl propylene diamine, N-stearyl propylene diamine, glycine ethyl ester, methyl 3-dimethylaminopropionate, tetrabutyl ammonium acetate, tetramethyl ammonium carbonate, stearylpyridinium hydroxide, cetyl dimethyl benzyl ammonium hydroxide, dimethyl morpholinium sulfide, dodecyl trimethyl ammonium formate, oleyl triethyl ammonium hydroxide, methyl ethyl isopropyl isobutyl ammonium hydrosulfide and choline bicarbonate.

The concentration of weakly basic amine catalyst can be rather small. As little as 0.1% is effective. The amount can extend up to 10%, although such large amounts are not normally required. A preferred amount is within the range from about 0.2% to about 3%. In the case of ammonia, from 1 to 2% is preferred.

It has been previously considered that an aqueous phase is essential to proper catalyst solubility. However, such use of aqueous systems has made the production of mercaptans from acrylic acid esters and hydrogen sulfide impossible. In the process mercaptans in substantial yields are obtained using as the solvent a dithiodipropionic acid ester or polythiodipropionic acid ester or mixture thereof. Since no aqueous phase is required, hydrolysis of the raw material and of the product, thus reducing yields, does not take place. In the instant process, the reaction medium is a single phase of dithio and/or polythio dipropionic acid ester, in which the acrylic ester, hydrogen sulfide and sulfur are dissolved. If mercaptans or dithiodipropionic acid esters are desired, the reaction medium solvent should be dithiodipropionic acid ester; if trisulfide dipropionic acid ester is desired, the reaction medium solvent should be trisulfide dipropionic acid ester, etc. A small amount of water (to keep catalyst in solution) may be used, insufficient to lead to hydrolysis. The amount of water is less than 5% and preferably less than 2.5%; the system is essentially nonaqueous. If a gas phase catalyst is used, no water need be present to dissolve catalyst.

Since the system is essentially nonaqueous, there is no disposal problem, such as occurs with aqueous systems containing ammonium mono or polysulfides or sodium sulfide derivatives. The reaction mixture can be worked up in a single distillation that yields both primary components in 90% or purer form, the mercaptan as distillate, and the dithio and/or polythio dipropionic acid ester as still bottoms.

The following process details are for a high-yield system for preparing either mercaptopropionic acid ester or dithiodipropionic acid ester.

A reaction medium of dithiodipropionic acid ester is provided.

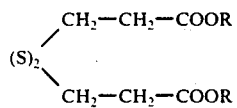

Hydrogen sulfide gas is bubbled into and dissolved therein to within the range from about an at least 0.1% by weight concentration up to the saturation point (about 2-3% by weight, at atmospheric conditions). Slight heat may be added but the reaction will proceed at any temperature within the range from 0 to 150° C. In any case, the temperature should be below about 75° C, and above about 0° C. The pressure on the system is determined mainly be the concentration of dissolved H₂S desired, and is not critical. Pressures of hydrogen sulfide of from 200 to 500 psig. can be used. Atmospheric pressure can be used at the lower H₂S concentrations.

To this reaction medium one or more acrylic acid esters CH₂ = CH — COOR are added at about 1 lb./hr./gal. reaction medium. The rate of addition should not exceed 10 lb./hr./gal., since local excesses of acrylic ester are to be avoided. R is hydrocarbon, e.g. alkyl, having from one to eight carbon atoms. It is possible to use mixed esters if asymmetric dithio and/or polythio dipropionic acid esters are desired, or if mixed mercaptopropionic acid esters are desired.

A weakly basic amine is added in an amount to give alkaline conditions for the reaction. Preferably, $NH_3$ is used, but also primary amines (e.g. monoethanolamine) or quaternary amines can be used. In addition $NH_3$ can be in the form of an aqueous ammonium hydroxide solution, added separately or added to either the medium containing $H_2S$ or to the acrylic ester. From 0.1 to 10% by weight of base is used, preferably 1% in the case of $NH_3$.

As the reaction begins the mercaptopropionic acid ester is formed; $H S - CH_2 - CH_2 - COOR$. If this is the intended end product, the temperature should be maintained at from 0° to 40° C, and the acrylic acid ester should be added slowly (under 1 lb./hr./gal.), with stirring. If the $H_2S$ concentration in the reaction medium is increased by increasing the $H_2S$ pressure to from about 75 to about 125 psig in a closed system, faster addition rates can be employed, e.g., up to 10 lb./hr./gal.

The mercaptopropionic acid ester produced can be easily removed as product from the reaction medium by distillation as it is formed, or shortly thereafter.

If it is desired to produce dithi or polythio dipropionic acid ester as products, the mercaptopropionic acid ester is left in the reaction medium, and sulfur is added. The concentration of mercaptopropionic acid ester should be kept below 50% by weight, preferably from about 7.5 to about 30%. A higher reaction temperature, lower $H_2S$ pressure, and faster acrylic acid ester addition can be used to favor formation of the dithio or polythio dipropionic acid ester.

The higher polythiodipropionic acid esters are prepared by addition of the appropriate stoichiometric amount of elemental sulfur.

While the crude dithiodipropionic acid ester is subject to many different possible procedures for upgrading to 94% minimum assay, the preferred procedure is to maintain a mercaptopropionic acid ester content in the crude, such that the molar ratio of mercaptopropionic acid ester to excess sulfur is 2:1 or more, heating until the excess sulfur is below 0.25%, and then adding dilute hydrogen peroxide in an at least stoichiometric amount in relation to the residual mercaptopropionic acid ester. Excess sulfur is defined as the total weight percent sulfur less the theoretical weight percent sulfur for the polythiodipropionic acid ester in question.

The products produced have a variety of uses. The dithiodipropionic acid and its esters are known to be useful in forming biologically active pesticides (see U.S. Pat. No. 2,719,170), and the mercaptan products can, of course, be used to produce the dithio compounds according to this invention, or can be converted to the monothiodiacid ester by known methods and thus be used to prepare antioxidants for polyolefins (see U.S. Pat. No. 3,501,520).

The following Examples, in the opinion of the inventors, represent preferred embodiments of their invention:

EXAMPLE 1

Batch production of mercapto propionic acid ester 605 grams of dimethyldithiodipropionate (DDD) was placed in a reactor and $H_2S$ gas was bubbled through it to maintain saturation conditions. The temperature of the liquid was maintained between 30° and 35° C. 12 ml of aqueous $(NH_4)_2S$ (25% $NH_3$) catalyst solution was added. 130 ml of methyl acrylate was introduced at a rate of 1 ml per 2 minutes through a sparger into the liquid, which was kept well agitated. After all of the methyl acrylate had been added, reaction was continued at 30° to 35° C for 1 hour.

Initial composition of DDD = 0.2% RSH (mercaptan). The final reaction mixture (undistilled) analyzed 18.2% -SH (as methyl mercapto propionate, i. e., MMp) after stripping dissolved $H_2S$. Conversion of methyl acrylate to MMP is about 92%.

EXAMPLE 2

Batch production of dithiodipropionic acid ester

The reactor was filled with 500 ml of a liquid reaction medium consisting of dimethyldithiodipropionate containing in solution small amounts of $H_2S$, ammonia, dimethylmonothiodipropionate, methylmercaptopropionate, and sulfur. Such a mixture was obtained from a previous batch of dithiodipropionic acid ester preparation. 28 grams of flowers of sulfur was slurried in this liquid, which was kept agitated, and the sulfur dissolved in a short period. Additional catalyst (25% aqueous $NH_3$ equal to 2% volume of methyl acrylate) was added. $H_2S$ gas was introduced continuously into the liquid through a sparger at a rate sufficient to maintain saturation conditions. The liquid was maintained at a temperature below 20° C by the circulation of cold water in the cooling coils of the reactor.

145 ml of methyl acrylate was added to the liquid through a sparger at a rate of about 1 ml/minute. This maintained the temperature below 20° C. Reaction was continued for one-half hour at below 20° C.

Reaction was continued for ½ hour at below 20° C. The contents of the reactor were drained to the 500 ml level at the end of methyl acrylate. A further 28 grams of sulfur was slurried, and the above process repeated- viz addition of catalyst and methyl acrylate.

The reaction mixture was then worked up by stripping off the volatiles. Total nonvolatile product collected = 380 grams of sp. gr. 1.242 at 25° C. This product after purification met the specifications of dimethyldithiodipropionate. The yield was 93% based on methyl acrylate.

EXAMPLE 3

Continuous production of dithiodipropionic acid ester

Continuous production of crude DDD was made in a reactor of 300 gallons capacity which contained an initial charge of DDD with 1% aqueous $NH_3$ catalyst. Methyl acrylate was added at a rate below 10 lb./hr./gal. $H_2S$ was introduced continuously into the charge at predetermined rates to maintain $H_2S$ saturation, while elemental sulfur (0.55 mole per mole methyl acrylate) and catalyst $(NH_4)_2S$ (as needed to maintain 1% $NH_3$ in solution) were added at ½ hour intervals. Cooling of the reactor contents to 30° C or below was done by circulating it through an external cooler. The product flowed through the reactor at a rate to give a residence time of at least 5 hours, and was drawn off continuously to the storage tank through a side draw-off, while maintaining a constant liquid level in the reactor. The excess $H_2S$ introduced escaped from the reaction through the vent line to a scrubbing system, for recovery.

The composition of the reaction product (after it was stripped of its catalyst and dissolved $H_2S$) was controlled by altering the ratio of reactants. 1

It was possible in this way to produce crude dithiodipropionic acid eser in 99% yield having less than 2% methylmercaptopropionate, and a total sulfur content in the range of 29 to 32%. This product when purified further yielded 96% of a product of 27.6 – 28% sulfur content.

A reaction product with high methylmercaptopropionate (15 – 20%) content was obtaind when the level of sulfur addition was reduced to 0.05 mole per mole methyl acrylate. The methylmercaptopropionate can be recovered by distillation, and the residue left after distillation recycled to the reactor. This continuous production methylmercaptopropionate can be achieved with a minimum of elemental sulfur, and in 90% yield, with the total yield of methyl mercaptopropionate and dimethyl dithio dipropionate being 99%.

EXAMPLE 4

Nonaqueous Synthesis of n-Dibutyl Dithiodipropionate From n-Butyl Acrylate, H₂S gas, and Sulfur in a Reaction Medium of n-Dibutyl Polythiodipropionate Preparation of n-Dibutyl Polythiodipropionate Reaction Medium:

Crude n-Dibutyl Polythiodipropionate

Sequence of Reaction

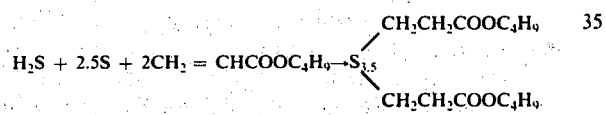

The reactor was a glass cylinder 12 inches high and 3.5 inches diameter, with a built-in cooling coil. Situated near the lower end of the reactor were H₂S and acrylic acid ester inlet tubes, a thermometer well, and a spout for product take-off. The reactor was topped with a ground glass 24/40 joint, which could accommodate a powder funnel, stopper or vent. The reaction medium was agitated by means of a magnetic stirrer.

Procedure

The clean and dry reactor was charged with 504 g. of crude n-dibutyl polythiodipropionate. Next, 4 ml of aqueous (NH₄)₂S solution was added to serve as catalyst for the reaction. Water was cuculated through the cooling coil, and agitation was started. The necessary connections to the H₂S cylinder and to a graduated dropping funnel containing the n-butyl acrylate were made. H₂S began at a rate of 700 – 950 ml per minute. After 15 minutes, the medium was saturated with H₂S and 0.55 mol (17.6 g) of sulfur was added and the medium was agitated for 5.0 minutes. The first mol of n-butyl acrylate (128 g) was added in 10 ml increments. The reaction temperature was maintained at 37° C – 38° C. After the addition of the first mol of acrylate was completed, a second 0.55 mol portion of sulfur (17.6 g) was added. After agitating 5 minutes, addition of the second mol of n-butyl acrylate was begun, 10 ml at a time. Since there was no noticeable rise in temperature, the catalyst was replenished by adding a second 4 ml portion of (NH₄)₂S solution. The temperature then rose from 25° C to 33° C and was maintained at 30° C – 33° C. After the second mol of acrylate was added, a third 0.55 mol (17.6 g) sulfur was added, and the medium was agitated for 5 minutes and then addition of the third mol of acrylate begun at 10 ml per increment. The temperature range was 27° C – 28° C. Approximately 27 grams excess of n-butyl acrylate was added. The addition of the acrylate took 3.5 hours. Thereafter, H₂S flow and agitation was continued for an additional 30 minutes, and then the product was poured into a clean tared bottle.

```
Total weight of product  = 1004 g
Weight of initial charge =  506 g
                            500 g weight of product synthesized
                           + 19 g withdrawn for testing at midway point
Weight of product prepared 519 g
```

The entire amount of butyl acrylate was converted to the di-n-butyl polythiodipropionate resulting in a 100% yield.

Comparison I with prior art aqueous system

Aqueous Synthesis of Diethyl Dithiodipropionate from Ethyl Acrylate,

Ammonium Sulfide and Sulfur

Step I. Preparation of Diethyl Polythiodipropionate

Sequence of reactions:

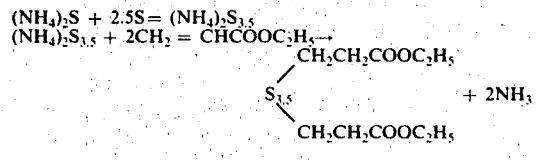

Procedure for preparing 1.5 mols of product 3 mols of ethyl acrylate = 300.33 g
1.8 mols of H₂S = 61.3 g
4.5 mols of sulfur = 144.3.

A 5 liter three-necked round bottom flask was set up in an icewater bath, and the flask was fitted with a finger was fitted with a finger agitator, a thermometer to measure liquid temperature, and a powder funnel for the introduction of sulfur.

508 cc of distilled water was placed in the flask and 309.1 grams of (NH₄)₂S solution assaying 19.83% H₂S was added. (The strength of H₂S in this solution was now approximately 7.5%).

Agitation was started and when the solution in the flask had cooled to 8° C, 144.3 grams of sulfur was added through the powder funnel, in 15 – 20 gram increments; each increment was allowed to dissolve, before adding the next. The liquid temperature ranged between 8° C – 10° C during the sulfur addition. The medium was agitated for an hour after the last increment of sulfur was added, until all the sulfur appeared to be completely dissolved. A dropping funnel was substituted for the powder funnel, and the dropwise addition of ethyl acrylate was started while the liquid temperature was held between 10° C – 15° C. The addition of the ethyl acrylate took 3.5 hours, and thereafter agitation was maintained for an additional 45 minutes. The reaction mixture was then poured into a separatory funnel and the layers allowed to separate. The organic layer (lower layer) was withdrawn into a tared clean 32 ounce bottle.

The weight of crude organic layer was 487.5 g which could be purified to yield 330 g of final product, a yield much lower than this invention.

Comparison II with prior art aqueous system

Synthesis of n-Dibutyl Polythiodipropionate from n-Butyl Acrylate, Ammonium

Sulfide and Sulfur in Aqueous medium

Preparation of n-Dibutyl Polythiodipropionate

Sequence of reactions $(NH_4)_2S + 2.5S = (NH_4)_2S_{3.5}$
$(NH_4)_2S_{3.5} + 2CH_2 = CHCOOC_4H_9 \rightarrow$

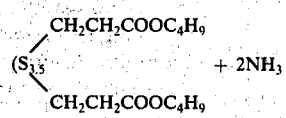

$+ 2NH_3$

Procedure for preparing 1.5 mols of product 3.0 mols of n-Butyl Acrylate = 384.1 g
1.8 mols of $H_2S$ = 61.3 g
4.5 mols of Sulfur = 144.3 g.

The flask and equipment used in Example 4 were used herein.

553 cc. of distilled water and 264.1 grams of $(NH_4)_2S$ solution assaying 23.21% $H_2S$ were added as in Comparison I. This made the $H_2S$ concentration approximately 7.5%. Agitation and addition of sulfur were as in Comparison I, except that initially the temperature was 10° C, and the liquid temperature range during addition was 10° – 15° C.

The powder funnel was replaced by a dropping funnel containing the n-butyl acrylate. With agitation, and the liquid temperature at 10° C., the dropwise addition of the 384.1 g of n-butyl acrylate was started, while keeping the liquid temperature between 10°– 15° C. The n-butyl acrylate was added over a period of 3.5 hours, and the reaction mixture agitated for an addition 45 minutes.

The reaction mixture was poured into a separatory funnel, and the layers allowed to separate. The lower organic layer was withdrawn into a clean tared 32 ounce bottle.

The weight of crude organic layer was 566.5 g which was purified to yield 409 g of final product, which is much below the yield of this invention.

EXAMPLE 5

For comparison purposes, a number of solvents were used for the preparation of methyl mercaptopropionate in a batch system.

The series of reactions studied showed the effect of the solvent on the formation of methylmercaptopropionate. The reactions were run under the conditions shown in the Table. The reaction mixtures were stirred for 2 hours at 25°– 30° C after the addition of methyl acrylate was completed, and then heated to 105° with venting to remove catalyst.

The results are given in Table I.

TABLE I

FORMATION OF METHYL MERCAPTOPROPIONATE IN VARIOUS SOLVENTS

| Solvent | $H_2S$ Pressure (psig) | Amine Base | Methyl mercaptopropionate Theoretical % in Product Mixture (Based on methyl acrylate added) | % Yield |
|---|---|---|---|---|
| Dimethyl monothio dipropionate | 77 | $NH_3$ | 10 | 70 |
|  |  |  | 20 | 60 |
|  |  |  | 32 | 59 |
|  |  |  | 42 | 52 |
|  |  |  | 53 | 45 |
| Methanol | 45 | $NH_3$ | 25 | 63 |
|  |  |  | 50 | 42 |
| Methyl mercaptopropionate | 45 | $NH_3$ | 25 | 12 |
|  |  |  | 50 | 20 |
| Dimethyl dithio dipropionate | 8 | $NH_3$ | 25 | 91 |
|  |  |  | 50 | 78 |
|  | 43 | $NH_3$ | 25 | 98 |
|  |  |  | 50 | 95 |
|  | 43 | $Et_3N$ | 50 | 99 |

It is apparent from the above results that dimethyl dithiodipropionate is exceptional, and gives yields up to 98%. The effect is one of a reactive solvent, strongly influencing the course of the reaction in favor of methylmercaptopropionate. It is surprising that methylmercaptopropionate and dimethylmonothiodipropionate are relatively ineffective. Indeed, methylmercaptopropionate seems to exert a depressing effect on yield, compared to, for instance, methanol, suggesting it displaces the equilibrium reactions in the wrong direction, and favoring conversion of methyl mercaptopropionate to dimethyl monothio dipropionate via reaction (2).

EXAMPLE 6

The preparation of methyl mercaptopropionate in a batch system in a series of reactions was carried out to show the effect of pressure on the formation of by-product dimethyl monothio dipropionate. Two reactions were run at 8 psig $H_2S$, giving theoretical final concentrations of 20 and 50% methyl mercaptopropionate, and one was run at 75 psig $H_2S$ to a final concentration of 50% methyl mercaptopropionate. The reaction mixtures were stirred for two hours at 25° – 30° C after the addition of methyl acrylate was completed, and then heated to 105° with venting to remove catalyst. Subsequent analysis of the reaction mixtures by gas liquid chromatographic analysis, corrected for retention factors, showed that the addition at 75 psig gave less dimethyl monothio dipropionate than the same addition at 8 psig (Table II).

TABLE II

| | COMPOSITION OF REACTION MIXTURES (grams) | | | | | |
|---|---|---|---|---|---|---|
| | Dimethyl dithio dipropionate[1] | NH$_4$OH | Methyl acrylate | H$_2$S Pressure psig | Temp (° C) | Weight of Reaction Product (grams) |
| (a) | 298.7 | 2.7 | 53.8 | 8 | 21–30° | 368 |
| (b) | 299.2 | 2.7 | 215.2 | 8 | 25–34° | 568.5 |
| (c) | 300.2 | | 71 | 75 | 25–30° | 374 |

| | COMPOSITION OF REACTION PRODUCT (% of total) | | | | |
|---|---|---|---|---|---|
| | Methyl mercaptopropionate Theoretical %[2] | Actual Yield % | Dimethyl monothio-dipropionate % | Dimethyl dithio-dipropionate % | Dimethyl polythio-dipropionate % |
| (a) | 20 | 14 | 3 | 76 | 7 |
| (b) | 50 | 34 | 8 | 58 | 0 |
| (c) | 50 | 38 | 2 | 60 | 0 |

[1]Analysis of dimethyl dithio dipropionate used as solvent:
6% methyl mercaptopropionate
2% dimethyl monothio dipropionate
77% dimethyl dithiodipropionate
15% dimethyl polythiodipropionate
[2]Based on methyl acrylate added In fact, the addition of methyl acrylate to a final concentration (theoretical) of 50% at 75 psig formed less dimethyl monothio dipropionate than the addition of methyl acrylate to a final concentration (theoretical) of 20% at 8 psig. The theoretical final concentration of methyl mercaptopropionate was not reached in any case. This may be due to loss of methyl mercaptopropionate in heating to drive off catalyst. It is evident that the polysulfide present in the initial reaction mixture is being consumed, presumably in reaction (3) above.

The reactor was modified by installing a sampling tube in order to take samples during the course of the reaction to determine the amount of post-stirring necessary to completely consume the methyl acrylate present in the reaction mixture.

At 45 psig H$_2$S, using concentrated aqueous ammonia catalyst (1% of initial charge), all methyl acrylate is consumed 40 minutes after the addition is stopped at a final concentration of 50% methyl mercaptopropionate. Using 4% catalyst, only a trace of methyl acrylate is left after five minutes.

During this work it was observed that a sample of methyl mercaptopropionate-free dimethyl dithiodipropionate, taken after the reactor had been pressurized but before the addition of methyl acrylate was started, contained a considerable amount of methyl mercaptopropionate. This reaction was investigated at different H$_2$S pressures (Table III).

Table III

| H$_2$S Pressure psig | Methyl Mercaptopropionate % | Dimethyl dithio-dipropionate % | Dimethyl thio-dipropionate polysulfide % |
|---|---|---|---|
| 0 | — | 100 | — |
| 10 | 22 | 65 | 13 |
| 20 | 23 | 62 | 15 |
| 43 | 24 | 61 | 15 |
| 80 | 25 | 60 | 15 |

The formation of methyl mercaptopropionate and polysulfide from dimethyl dithiodipropionate indicates that the formation of dimethyl dithiodipropionate from methyl mercaptopropionate and sulfur is a reversible reaction, and that dimethyl dithiodipropionate is functioning not only as a solvent but is also participating in the reaction.

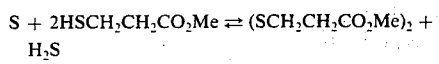

S + 2HSCH$_2$CH$_2$CO$_2$Me ⇌ (SCH$_2$CH$_2$CO$_2$Me)$_2$ + H$_2$S

This confirms the reaction mechanism, as outlined as above.

Having regard for the foregoing disclosure, the following is claimed as the inventive and patentable embodiments thereof:

1. A process for the preparation of at least one reaction product selected from the group consisting of mercaptopropionic acid esters of the formula:

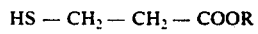

HS — CH$_2$ — CH$_2$ — COOR and polythiodipropionic acid esters of the formula:

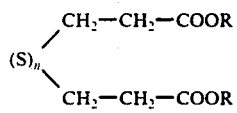

$$(S)_n\diagup\diagdown\begin{array}{l}CH_2-CH_2-COOR\\ CH_2-CH_2-COOR\end{array}$$

wherein n is a number from 2 to 10 and R is selected from the group consisting of alkyl, cycloalkyl, and alkyl cycloalkyl having from one to about eight carbon atoms which comprises reacting hydrogen sulfide and an acrylic acid ester of the formula:

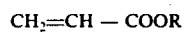

CH$_2$=CH — COOR wherein R is selected from the group consisting of alkyl, cycloalkyl, and alkyl cycloalkyl having from one to about eight carbons atoms, and elemental sulfur in an amount within the range from about 0.01 to about 5 moles per mole of acrylic acid ester in an essentially nonaqueous system containing less than 5% water and in the presence of a reactive solvent comprising polythiodipropionic acid ester of the formula above; the polythiodipropionic acid ester being present in an amount of at least 30% by weight of the total of any monothiodipropionic acid ester and of the polythiodipropionic acid ester present; a weakly basic amine catalyst selected from the group consisting of ammonia, primary, secondary, and tertiary amines and quaternary amines; the weakly basic amine catalyst being present in an amount within the range from about 0.1 to about 10% by weight of the reaction mixture; the reaction being carried out at a temperature within the range from about 0 to about 150° C and an H$_2$S concentration within the range from about 0.1% to saturation in the reactive solvent under the reaction conditions; and recovering at least one reaction product selected from the group consisting of mercaptopropionic acid ester and polythiodipropionic acid ester from the resulting reaction mixture.

2. A process in accordance with claim 1, in which hydrogen sulfide is dissolved in the polythiodipropionic acid ester and the acrylic acid ester is added to the resulting solution at a rate of up to about one pound per hour per gallon of solution.

3. A process in accordance with claim 1, in which $H_2S$ is dissolved in the lythiodipropionic acid ester, the pressure of hydrogen sulfide is maintained within the range from about 75 to about 125 psig and acrylic acid ester is added to the resulting solution at a rate of up to about 10 pounds per hour per gallon of solution.

4. A process in accordance with claim 1, in which the catalyst is ammonia.

5. A process in accordance with claim 4, in which the ammonia is added as ammonium sulfide.

6. A process in accordance with claim 1, in which elemental sulfur is added to the solution in an amount within the range from about 0.05 to about 5 moles per mole of acrylic acid ester sufficient to increase the amount formed of polythiodipropionic acid ester.

7. A process in accordance with claim 6, in which the amount of elemental sulfur is within the range from about 0.5 to about 4.5 moles per mole of acrylic acid ester.

8. A process in accordance with claim 6, in which the content of mercaptopropionic acid ester is kept below 50% by weight of the solution.

9. A process in accordance with claim 1, in which elemental sulfur is added in an amount within the range from about 0.01 to about 0.5 mole per mole of acrylic acid ester sufficient to increase the amount formed of mercaptopropionic acid ester.

10. A process in accordance with claim 9, in which the amount of elemental sulfur is within the range from about 0.03 to about 0.05 mole per mole of acrylic acid ester.

11. A process in accordance with claim 1, in which the hydrogen sulfide pressure above the reactive solvent is maintained within the range from about atmospheric pressure to about 500 psig in a closed system.

12. A process in accordance with claim 1, in which the mercaptopropionic acid ester is separated from the reaction mixture by distillation.

13. A process in accordance with claim 12, in which a polythiodipropionic acid ester is recovered as still bottoms following distillation of mercaptopropionic acid ester.

14. A process in accordance with claim 13 in which polythiodipropionic acid ester recovered as still bottoms is recycled as solvent for further reaction of acrylic acid ester with hydrogen sulfied.

15. A process in accordance with claim 14, in which the addition of hydrogen sulfide and acrylic acid ester is carried out continuously, and the reaction mixture comprising reaction product is withdrawn continuously and separated by distillation into mercaptopropionic acid ester and polythiodipropionic acid ester.

16. A process in accordance with claim 1, in which the amount of hydrogen sulfide is in excess of the stoichiometric ratio 1:1 up to 5:1 $H_2S$ to acrylic acid ester.

17. A process in accordance with claim 16, in which the reaction temperature is within the range from about 0° to about 40° C.

18. A process in accordance with claim 1, in which the amount of hydrogen sulfide is in the ratio of 0.5:1 to 1:1 $H_2S$ to acrylic acid ester.

19. A process in accordance with claim 18 in which the reaction temperature is within the range from about 75° to about 150° C.

20. A process in accordance with claim 1 in which the acrylic acid ester is methyl acrylate, and the polythiodipropionic acid ester is dimethyl dithiodipropionate.

21. A process in accordance with claim 1, in which the weakly basic amine catalyst is an amine.

22. A process in accordance with claim 21 in which the amine is a primary amine.

23. A process in accordance with claim 21, in which the amine is a secondary amine.

24. A process in accordance with claim 21, in which the amine is a tertiary amine.

25. A process in accordance with claim 21, in which the amine is a quaternary ammonium compound.

* * * * *

UNITED STATES PATENT OFFICE
CERTIFICATE OF CORRECTION

Patent No. 4,067,901    Dated January 10, 1978

Inventor(s) Shaul Gladstone et al.

It is certified that error appears in the above-identified patent and that said Letters Patent are hereby corrected as shown below:

| | | |
|---|---|---|
| Column 2, line 20 | : | before "eight" insert --about-- |
| Column 2, line 35 | : | "mercaptopropinic" should be --mercaptopropionic-- |
| Column 3, line 41: | : | "dithiopropionic" should be --dithiodipropionic-- |
| Column 3, line 55 | : | "dithiopropionic" should be --dithiodipropionic-- |
| Column 4, line 6 | : | "solythiodipropionic" should be --polythiodipropionic-- |
| Column 5, line 54 | : | "reaction" first occurrence should be --reactive-- |
| Column 6, line 56 | : | before "eighteen" insert --about-- |
| Column 7, lines 6 & 7: | : | "tertiary-octy" should be --tertiary-octyl-- |
| Column 8, line 54 | : | "be" should be --by-- |
| Column 9, line 22 | : | "dithe" should be --dithio-- |
| Column 10, line 6 | : | "MM" should be --MMP-- |

UNITED STATES PATENT OFFICE
CERTIFICATE OF CORRECTION

Patent No. 4,067,901                    Dated January 10, 1978

Inventor(s) Shaul Gladstone et al.

It is certified that error appears in the above-identified patent and that said Letters Patent are hereby corrected as shown below:

| | |
|---|---|
| Column 10, line 33 | delete "Reaction was continued for 1/2 hour at below 20°C."; this is a repeat of lines 30 to 31 |
| Column 10, line 68 | after "reactants." delete --1-- |
| Column 11, line 19 | before "methylmercaptopropionate" insert --of-- |
| Column 11, line 53 | "cuculated" should be --circulated-- |
| Column 11, line 57 | after "H$_2$S" insert --flow-- |
| Column 12, line 43 | after "144.3" inert --g-- |
| Column 12, line 47 | delete "was fitted with a finger" |
| Column 13, lines 16, 17, & 39-4 | " $(NH_4)_2S_{3.5} + 2CH_2 = CHCOOC_4H_9 \rightarrow$ | should be

-- $(NH_4)_2S_{3.5} + 2CH_2 = CHCOOC_4H_9 \rightarrow$ 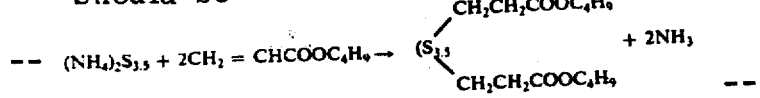 --

UNITED STATES PATENT OFFICE
CERTIFICATE OF CORRECTION

Patent No. 4,067,901          Dated January 10, 1978

Inventor(s) Shaul Gladstone et al.

It is certified that error appears in the above-identified patent and that said Letters Patent are hereby corrected as shown below:

Column 13, line 65 : "addition" should be --additional--

Column 15, Table III, line 51, Fourth column : "thio" should be --dithio--

Column 17, line 7 : "lythiodipropionic" should be --polythiodipropionic--

Column 18, line 11 : "sulfied" should be --sulfide--

Signed and Sealed this

Fourth Day of July 1978

[SEAL]

Attest:

RUTH C. MASON
Attesting Officer

DONALD W. BANNER
Commissioner of Patents and Trademarks